US007674589B2

(12) United States Patent
Cohen et al.

(10) Patent No.: US 7,674,589 B2
(45) Date of Patent: *Mar. 9, 2010

(54) METHODS FOR TISSUE ANALYSIS

(75) Inventors: Robert L. Cohen, San Mateo, CA (US); Mary Beth Gardiner, Nashville, TN (US); Mark X. Sliwkowski, San Carlos, CA (US); Gregory T. Stelzer, Brentwood, TN (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/331,178

(22) Filed: Dec. 9, 2008

(65) Prior Publication Data

US 2009/0155803 A1 Jun. 18, 2009

Related U.S. Application Data

(63) Continuation of application No. 11/925,634, filed on Oct. 26, 2007, now Pat. No. 7,468,252, which is a continuation of application No. 11/399,737, filed on Apr. 6, 2006, now Pat. No. 7,344,840, which is a continuation of application No. 10/978,033, filed on Oct. 29, 2004, now Pat. No. 7,129,051, which is a continuation of application No. 10/351,067, filed on Jan. 23, 2003, now Pat. No. 6,905,830, which is a continuation of application No. 09/167,691, filed on Oct. 7, 1998, now Pat. No. 6,573,043.

(51) Int. Cl.
 C12Q 1/68 (2006.01)
 G01N 33/53 (2006.01)
(52) U.S. Cl. .......................... 435/6; 435/7.1
(58) Field of Classification Search .................. 435/6, 435/7.1
 See application file for complete search history.

(56) References Cited

U.S. PATENT DOCUMENTS

| 4,968,603 | A | 11/1990 | Slamon et al. | 435/6 |
|---|---|---|---|---|
| 5,660,982 | A | 8/1997 | Tryggvason et al. | 435/6 |
| 5,726,023 | A | 3/1998 | Cheever et al. | 435/7.1 |
| 5,846,749 | A | 12/1998 | Slamon et al. | 435/7.23 |
| 5,876,712 | A | 3/1999 | Cheever et al. | 424/93.7 |
| 6,027,890 | A | 2/2000 | Ness et al. | 435/6 |

FOREIGN PATENT DOCUMENTS

| EP | 801306 A | 10/1997 |
|---|---|---|
| FR | 2711671 A | 5/1995 |
| WO | WO 94/00764 | 1/1994 |
| WO | WO 94/09022 | 4/1994 |
| WO | WO 95/03428 | 2/1995 |
| WO | WO 96/31626 | 10/1996 |
| WO | WO 97/08343 | 3/1997 |
| WO | WO 98/02577 | 1/1998 |
| WO | WO 00/31534 | 2/2000 |

OTHER PUBLICATIONS

Anastasi et al., "Cytogenetic clonality in myelodysplastic syndromes studied with fluorescence in situ hybridization: linege, response to growth factor therapy, and clone expansion" *Blood* 81(6), 1580-1585 (Mar. 15, 1993).
Anastasi, et al., "Detection of trisomy 12 in chronic lymphocytic leukemia by fluorescence in situ hybridization to interphase cells: a simple and sensitive method" *Blood* 79(7), 1796-1801 (Apr. 1, 1992).
Anastasi, et al., "Direct correlation of cytogenetic findings with cell morphology using in situ hybridization: an analysis of suspicious cells in bone marrow specimens of two patients completing therapy for acut lymphoblastic leukemia" *Blood* 77(11), 2456-2462 (Jun. 1, 1991).
Anastasi, et al., "The relationship between secondary chromosomal abnormalities and blast transformation in chronic myelogenous leukemia" *Leukemia* 9(4), 628-633 (Apr. 1995).
Clark, et al., "Follow-up study of HER-2/new amplification in primary breast cancer" *Cancer Research* 51(3); 944-948 (Feb. 1, 1991).
DAKO Corporation, "DAKO Anti-HER2 IHC System for Immunoenzymatic Staining" (Package Insert) pp. 1-12, (1990).
Fendly, et al., "Characterization of Murine Momoclonal Antibodies Reactive to Either the Human Epidermal Growth Factor Receptor or HER2/new Gene Product" *Cancer Research*, 50, 1550-1558 (Mar. 1, 1990).
Heintz, et al., "Amplification of the c-erb B-2 oncogene and prognosis of breast adenocarcinoma" *Archives Of Pathology & Laboratory Medicine*, 114(2), 160-163 (Feb. 1990).
Jenkins, et al., "Fluorescene in situ hybridization: a sensitive method for trisomy 8 detection in bone marrow specimens" *Blood*, 79(12), 3307-3315 (Jun. 15, 1992).
Kury, et al., "HER-2 oncogene amplification and overall survival of breast carcinoma patients" *European Journal Of Cancer*, 26(9), 946-949 (1990).
McCann, et al., "Prognostic significance of c-erbB-2 amd estrogen receptor status in human breast cancer" *Cancer Research*, 51(12), 3296-3303 (Jun. 15, 1991).
Nelson, et al., "Comparison of HER-2/NEU Amplification Using Fluorescent In Situ Hybridization (FISH) with Immunohistochemically Determined Overexpression in Breast Cancers" *Modern Pathology*, 9(1), 21A (1996).
Paferson et al., "Correlation between c-erb-2 amplification and rish of recurrent disease in node-negative breast cancer" *Cancer Research*, 51(2), 556-567 (Jan. 15, 1991).
Pauletti et al., "Detection and quantitation of HER-2/neu gene amplification in human breast cancer archival material using fluorescence in situ hybridization" *Oncogene* 13(1), 63-72 (Jul. 4, 1996.

(Continued)

*Primary Examiner*—Kenneth R. Horlick
(74) *Attorney, Agent, or Firm*—Atulya R. Agarwal; James A. Fox; Ginger R. Dreger

(57) ABSTRACT

This invention relates to methods of analyzing a tissue sample from a subject. In particular the invention combines morphological staining and/or immunohistochemistry (IHC) with fluorescence in situ hybridization (FISH) within the same section of a tissue sample. The analysis can be automated or manual. The invention also relates to kits for use in the above methods.

24 Claims, 5 Drawing Sheets

OTHER PUBLICATIONS

Ravdin et al., Cathepsin D by western blotting and immunohistochemistry: failure to confirm correlations with prognosis in node-negative breast cancer *Journal Of Clinical Oncology*, 12(3), 467-474 (Mar. 1994).

Slamon, et al., "Human Breast Cancer: Correlation of Relapse and Survival with Amplification of the HER-2/new Oncogene" *Science*, 235, 177-182 (1987).

Slamon, et al., "Studies of the HER-2/neu Proto-oncogene in Human Breast and Ovarian Cancer" *Science*, 244, 707-712 (May 1989).

Tandon et al., "HER-2/neu oncogene protein and prognosis in breast cancer" *Journal of Clinical Oncology*, 7(8), 1120-1128 (Aug. 1989).

Van de Vijver, et al, "Neu-protein overexpression in breast cancer. Association with comedo-type ductal carcinoma in situ and limited prognostic value in stage II breast cancer" *New England J. of Medicine*, 319(19), 1239-1245 (Nov. 10, 1988).

Van Lom et al., "In situ hybridization on May-Grunwald Giemsa-stained bone marrow and blood smears of patients with hematologic disorders allows detection of cell-lineage-specific cytogenetic abnormalities" *Blood*, 82(3), 884-888 (Aug. 1, 1993).

Walker, et al., "An evaluation of immunoreactivity for c-erbB-2 protein as a marker of poor short-term prognosis in breast cancer" *Bristish Journal of Cancer*, 60(3), 426-429 (Sep. 1989).

Winstanley et al., "The long term prognostic significance of c-erbB-2 in primary breast cancer" *British Journal of Cancer*, 63(3), 447-450 (Mar. 1991).

Wolman, et al., "An approach to definition of genetic alterations in prostate cancer" *Diagnostic Molecular Pathology*, 1(3), 192-199 (Sep. 1992).

Wright, et al, "Expression of c-erbB-2 oncoprotein: a prognostic indicator in human breast cancer" *Cancer Research*, 49(8), 2087-2090 (Apr. 15, 1989).

Young et al., "Species-specific in situ hybridization with fluorochrome-labeled DNA probes to study vascularization of human skin grafts on athymic mice" *Journal of Burn Care & Rehabilitation*, 17(4), 305-310 (Jul.-Aug. 1996).

Zhou et al, "Proto-oncogene abnormalities in human breast cancer: c-ERBB-2 amplification does not correlate with recurrence of desease" *Oncogene*, 4(1), 105-108 (Jan. 1989).

Zitzelsberger, et al., "Numerical abnormalities of chromosome 7 in human prostate cancer detected by fluorescence in situ hybridization (FISH) on paraffin-embedded tissue sections with centromere-specific DNA probes" *Journal of Pathology*, 172(4), 325-335 (Apr. 1994).

Ng, et al., "Short Communication—Combined Morphological and Interphase Fluorescence in Situ Hybridization Study in Multiple Myeloma of Chinese Patients" *American Journal of Pathology*, 154, 15-22 (1999).

Gardiner, et al., "Development of a technique that allows simultaneous assessment of morphology and gene amplification by FISH: application to HER-2/Neu amplification in breast cancer" *Modern Pathology*, (abstract #1122) 12(1), 191A (Jan. 1999).

Press, et al., "Amplification and overexpression of HER-2/neu in carcinomas of the salivary gland: correlation with poor prognosis" *Cancer Research*, 54(21), 5675-5682 (Nov. 1, 1994).

Ratcliffe et al., "The combination of in situ hybridization and immunohistochemical analysis: and evaluation of Her2/neu expression in paraffin-embedded breast carcinomas and adjacent normal-appearing breast epithelium" *Modern Pathology*, 10(12), 1247-1252 (Dec. 1997).

MDA231　　　MDA175　　　SKBR3　　FISH Only

Stain & FISH

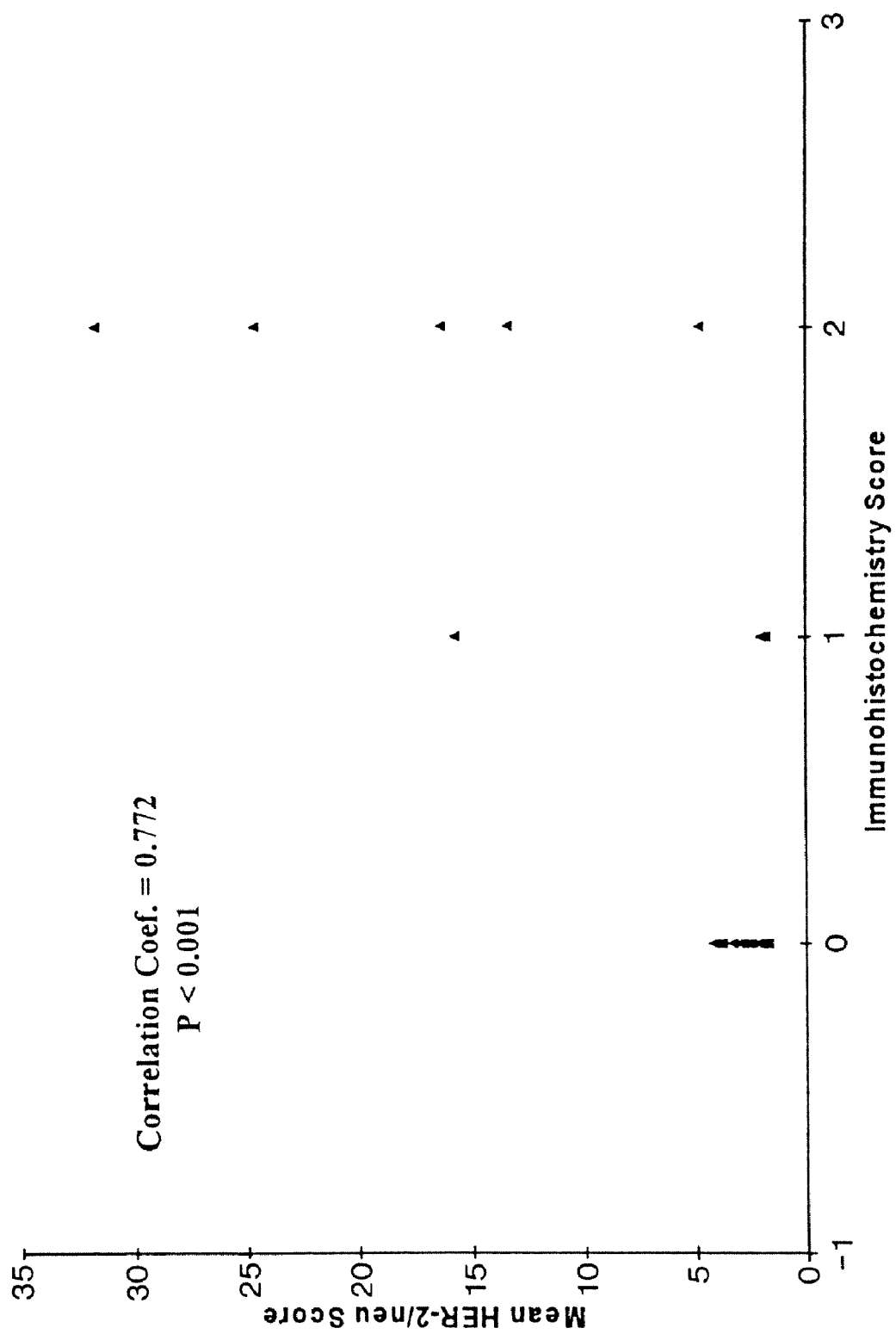

METHODS FOR TISSUE ANALYSIS

CROSS-REFERENCE TO RELATED APPLICATIONS

This application is a continuation application of U.S. application Ser. No. 11/925,634, filed on Oct. 26, 2007, now U.S. Pat. No. 7,468,252 which is a continuation application of U.S. application Ser. No. 11/399,737, filed on Apr. 6, 2006, now U.S. Pat. No. 7,344,840, which is a continuation application of U.S. application Ser. No. 10/978,033, filed Oct. 29, 2004, now U.S. Pat. No. 7,129,051, which is a continuation of U.S. application Ser. No. 10/351,067, filed Jan. 23, 2003, now U.S. Pat. No. 6,905,830, which is a continuation of U.S. application Ser. No. 09/167,691, filed Oct. 7, 1998, now U.S. Pat. No. 6,573,043, which applications are hereby incorporated herein by reference in their entireties and from which applications priority is claimed under 35 U.S.C. §120.

FIELD OF THE INVENTION

The present invention relates generally to the field of tissue analysis. Specifically, the invention combines morphological staining and/or immunohistochemistry (IHC) with fluorescence in situ hybridization (FISH) within the same section of a tissue sample thereby allowing for accurate and simplified prognostic, diagnostic, or research applications on a subject's tissue sample. In addition, the invention provides kits for analysis of a tissue sample utilizing the present methods.

BACKGROUND OF THE INVENTION

Advancements in the understanding of genetics and developments in technology and epidemiology have allowed for the correlation of genetic abnormalities with certain malignancies as well as risk assessment of an individual for developing certain malignancies. However, most of the methodologies available for evaluation of tissue for the presence of genes associated with or predisposing an individual to a malignancy have well-known drawbacks. For example, methods that require disaggregation of the tissue, such as Southern, Northern, or Western blot analysis, are rendered less accurate by dilution of the malignant cells by the normal or otherwise non-malignant cells that are present in the same tissue. Furthermore, the resulting loss of tissue architecture precludes the ability to correlate malignant cells with the presence of genetic abnormalities in a context that allows morphological specificity. This issue is particularly problematic in tissue types known to be heterogeneous, such as in human breast carcinoma, where a significant percentage of the cells present in any area may be non-malignant.

Fluorescence in situ hybridization (FISH) is a recently developed method for directly assessing the presence of genes in intact cells. FISH is an attractive means of evaluating paraffin-embedded tissue for the presence of malignancy because it provides for cell specificity, yet overcomes the cross-linking problems and other protein-altering effects caused by formalin fixation. FISH has historically been combined with classical staining methodologies in an attempt to correlate genetic abnormalities with cellular morphology [see e.g., Anastasi et al., *Blood* 77:2456-2462 (1991); Anastasi et al., *Blood* 79:1796-1801 (1992); Anastasi et al., *Blood* 81:1580-1585 (1993); van Lom et al., *Blood* 82:884-888 (1992); Wolman et al., *Diagnostic Molecular Pathology* 1(3): 192-199 (1992); Zitzelberger, *Journal of Pathology* 172:325-335 (1994)]. However, several of these studies address hematological disorders where genetic changes are assessed in freshly fixed smears from bone marrow aspirates or peripheral blood specimens. Of those two studies where paraffin-embedded tissue was analyzed, one involved evaluation of FISH and morphological staining on separate, serial sections. In the other study, both procedures were performed on the same section, but morphological staining was subsequent to evaluation by FISH. Use of serial sections in this type of analysis increases the probability of error, especially in heterogeneous tissue such as breast tissue.

Immunohistochemical staining of tissue sections has been shown to be a reliable method of assessing alteration of proteins in a heterogeneous tissue. Immunohistochemistry (IHC) techniques utilize an antibody to probe and visualize cellular antigens in situ, generally by chromagenic or fluorescent methods. This technique excels because it avoids the unwanted effects of disaggregation and allows for evaluation of individual cells in the context of morphology. In addition, the target protein is not altered by the freezing process.

The HER2/neu gene encodes a protein product, often identified as $p185^{HER2}$. The native $p185^{HER2}$ protein is a membrane receptor-like molecule with homology to the epidermal growth factor receptor (EGFR). Amplification and overexpression of HER2 in human breast cancer has been correlated with shorter disease-free interval and shorter overall survival in some studies [van de Vijer et al. *New Eng. J. Med.* 317:1239 (1988); Walker et al. *Br. J. Cancer* 60:426 (1989); Tandon et al. *J. Clin. Invest.* 7:1120 (1989); Wright et al. *Cancer Res.* 49:2087 (1989); McCann et al. *Cancer Res* 51:3296 (1991); Paterson et al. *Cancer Res.* 51:556 (1991); and Winstanley et al. *Br. J. Cancer* 63:447 (1991)] but not in others [Zhou et al. *Oncogene* 4:105 (1989); Heintz et al. *Arch Path Lab Med* 114:160 (1990); Kury et al. *Eur. J. Cancer* 26:946 (1990); Clark et al. *Cancer Res.* 51:944 (1991); and Ravdin et al. *J. Clin. Oncol.* 12:467-74 (1994)].

In an initial evaluation of 103 patients with breast cancer, those having more than three tumor cell positive axillary lymph nodes (node positive) were more likely to overexpress HER2 protein than patients with less than three positive nodes [Slamon et al. *Science* 235:177 (1987)]. In a subsequent evaluation of 86 node-positive patients with breast cancer, there was a significant correlation among the extent of gene amplification, early relapse, and short survival. HER2 overexpression was determined using Southern and Northern blotting which correlate with the HER2 oncoprotein expression evaluated by Western blotting and IHC [Slamon et al. *Science* 235:177 (1987); Slamon et al. *Science* 44:707 (1989)]. The median period of survival was found to be approximately 5-fold shorter in patients with more than five copies of the HER2 gene than in patients without gene amplification. This correlation was present even after correcting for nodal status and other prognostic factors in multivariate analyses. These studies were extended in 187 node-positive patients and indicated that gene amplification, increased amounts of mRNA (determined by Northern blotting), and increased protein expression (determined immunohistochemically) were also correlated with shortened survival time [Slamon et al. *Science* 244:707 (1989)]. See also U.S. Pat. No. 4,968,603 to Slamon et al Nelson et al. have compared HER2/neu gene amplification using FISH with immunohistochemically determined overexpression in breast cancer [Nelson et al. *Modern Pathology* 9(1) 21A (1996)].

SUMMARY OF THE INVENTION

The present invention combines cellular morphological analysis with fluorescence in situ hybridization (FISH) to provide for a correlation of genetic abnormalities and cellular morphology within the same section of a subject's tissue sample. Accordingly, one may identify and score by FISH cancer cells (e.g. invasive ductal carcinoma cells) as distinct from other normal cells (e.g. stromal and inflammatory elements found in the biopsy). Alternatively, or additionally, the invention combines immunohistochemistry (IHC) with FISH to provide for a correlation of genetic abnormalities with protein expression in the same tissue section.

Morphologic assessment, or evaluation of protein expression, in a tissue prior to quantitative FISH analysis provides for accurate, specific evaluation of that tissue in a timely and cost-efficient manner. Thus, there is a need in research, prognostic, and diagnostic applications for a method that can allow for morphologic and/or protein expression analyses followed by FISH assessment in a single tissue sample section, particularly when testing a heterogeneous tissue. The invention described in this disclosure offers these features.

Accordingly, in a first aspect the invention provides a method of correlating cellular morphology with the presence of a cellular target nucleic acid sequence in a section of a tissue sample comprising the following steps:

(a) staining the section of tissue sample with a morphological stain;

(b) determining cellular morphology in the section of tissue sample;

(c) hybridizing a first fluorescently labeled nucleic acid probe to the target nucleic acid sequence in the same section of tissue sample;

(d) detecting the presence of the first nucleic acid probe in the section of tissue sample; and (e) correlating step (b) with step (d).

In an alternative embodiment, the invention pertains to a method of correlating the presence of a cellular target protein with the presence of a cellular target nucleic acid sequence in a section of a tissue sample comprising the following steps:

(a) contacting the section of sample tissue with an antibody which specifically binds to the target protein;

(b) determining binding of the antibody to the section of tissue sample;

(c) hybridizing a fluorescently labeled nucleic acid probe to the target nucleic acid sequence in the same section of tissue sample;

(d) detecting the presence of the labeled nucleic acid probe in the section of tissue sample; and (e) correlating step (b) with step (d).

Additionally, the invention provides a kit comprising: (a) a morphological stain; (b) a fluorescently labeled probe complementary to a genetic abnormality; and (c) instructions for applying the stain (a) and probe (b) to the same section of tissue sample.

Moreover, a kit is provided comprising: (a) a primary antibody which specifically binds a cellular target protein; (b) a fluorescently labeled probe complementary to a genetic abnormality; and (c) instructions for applying the antibody (a) and probe (b) to the same section of tissue sample.

DESCRIPTION OF THE FIGURES

FIG. 5 shows the relationship between the scoring systems used for HER2/neu amplification by FISH and overexpression by IHC.

DETAILED DESCRIPTION OF THE INVENTION

Figure 1:
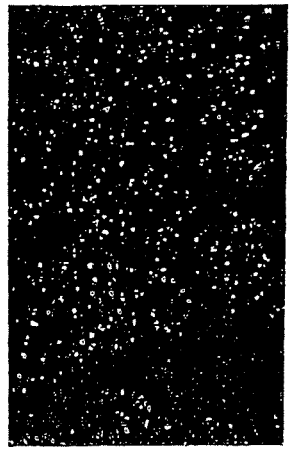
FIG. 1 shows the effect of HEMA 3® staining on the ability to score FISH in formalin fixed, paraffin-embedded cells harvested from each of three cell lines of known HER2/neu amplification status; SKBR3 (highly amplified HER2), MDA175 (barely amplified HER2), and MDA231 (non-amplified HER2).
Figure 1:
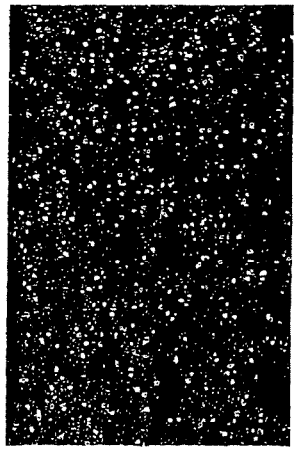
Figure 1:
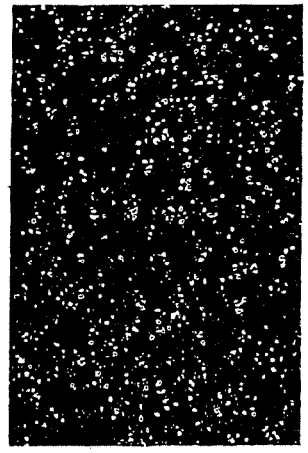
Figure 1:
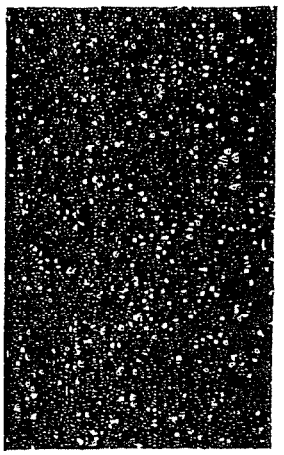
Figure 1:
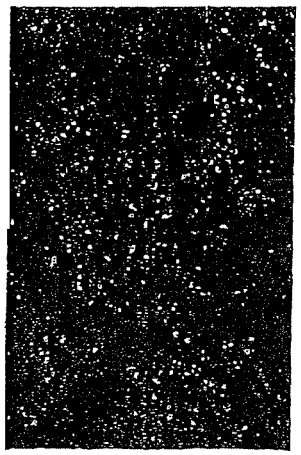

Before the present methods, kits and uses therefor are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a genetic alteration" includes a plurality of such alterations and reference to "a probe" includes reference to one or more probes and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference to disclose and describe the methods and/or materials in connection with which the publications are cited.

Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

DEFINITIONS by "subject" or "patient" is meant any single subject for which therapy is desired, including humans, cattle, dogs, guinea pigs, rabbits, chickens, insects and so on. Also intended to be included as a subject are any subjects involved in clinical research trials not showing any clinical sign of disease, or subjects involved in epidemiological studies, or subjects used as controls.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like. In one embodiment of the invention, the tissue sample is "non-hematologic tissue" (i.e. not blood or bone marrow tissue).

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present inventions provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. With respect to the embodiment of morphological analysis followed by FISH, one may use the results obtained upon morphological staining to determine area(s) of a tissue section which are normal and/or area(s) which are cancerous. Thus, histologically normal area(s) in a heterogeneous tumor biopsy may be used as internal normal control(s). In relation to IHC combined with FISH, one may use the results of IHC to determine whether FISH should be performed and/or one may compare the level of protein expression with gene amplification to further characterize a tumor biopsy (e.g. to compare HER2 protein expression with HER2 gene amplification).

By "nucleic acid" is meant to include any DNA or RNA. For example, chromosomal, mitochondrial, viral and/or bacterial nucleic acid present in tissue sample. The term "nucleic acid" encompasses either or both strands of a double stranded nucleic acid molecule and includes any fragment or portion of an intact nucleic acid molecule.

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

By "genetic abnormality" is meant a deletion, substitution, addition, translocation, amplification and the like relative to the normal native nucleic acid content of a cell of a subject.

By "disease gene" is meant a gene that results in altered protein product (i.e., protein different from native protein in terms of sequence, structure and/or amount expressed) and results in a disease.

By "deletion" is meant the absence of all or part of a gene.

By "amplification" is meant the presence of one or more extra gene copies in a chromosome complement.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The term "fluorescently labeled nucleic acid probe" refers to a probe comprising (1) a nucleic acid sequence capable of hybridizing with a target nucleic acid sequence and (2) a fluorescent label.

By "morphological stain" is meant a dye that stains different cellular components, in order to facilitate identification of cell type and/or disease status by light microscopy. Preferably, the morphological stain is readily distinguishable from any label used in the FISH analysis, e.g., a stain which will not autofluoresce at the same wavelength as the fluorochrome used in the FISH analysis.

The term "antibody" is used in the broadest sense and specifically covers monoclonal antibodies, polyclonal antibodies, multispecific antibodies (e.g., bispecific antibodies), and antibody fragments so long as they bind specifically to a target antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al. *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; and Morrison et al. *Proc. Natl. Acad. Sci. USA* 81:6851-6855 (1984)].

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding nonhuman residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

The term "primary antibody" herein refers to an antibody which binds specifically to the target protein antigen in a tissue sample. A primary antibody is generally the first antibody used in an immunohistochemical procedure. In one embodiment, the primary antibody is the only antibody used in an IHC procedure.

The term "secondary antibody" herein refers to an antibody which binds specifically to a primary antibody, thereby forming a bridge between the primary antibody and a subsequent reagent, if any. The secondary antibody is generally the second antibody used in an immunohistochemical procedure.

Unless indicated otherwise, the terms "HER2", "p185$^{HER2}$" and "ErbB2" when used herein refer to human HER2 protein or a portion thereof and "HER2", "HER2/neu" and "c-erbB2" refer to the human HER2 gene or a portion thereof. The human HER2 gene and HER2 protein are, for example, described in Semba et al., *PNAS (USA)* 82:6497-6501 (1985) and Yamamoto et al. *Nature* 319:230-234 (1986) (Genebank accession number X03363).

Dual Analysis Method

The present invention relates to a method which combines morphological staining and/or immunohistochemical analysis with fluorescence in situ hybridization (FISH) within the same section of a tissue sample. The present methods allow for a highly accurate and simplified method of correlating morphological criteria or protein expression with genetic abnormalities. Because many tissue types, such as breast tissue, are characterized by significant cellular heterogeneity, inaccurate results may be obtained when serial sections from a tissue block are analyzed by two different methods. According to the present invention, both types of analysis are carried out on the same tissue section, thereby reducing error when analyzing such heterogeneous tissue. As evidenced by the following, the method of this application is useful in a variety of prognostic, diagnostic and research applications. Also disclosed are kits for use in the disclosed methods.

Sample Preparation

Any tissue sample from a subject may be used. Examples of tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, the tissue sample is fixed and embedded in paraffin or the like.

The tissue sample may be fixed (i.e. preserved) by conventional methodology [See e.g., "Manual of Histological Staining Method of the Armed Forces Institute of Pathology," 3$^{rd}$ edition (1960) Lee G. Luna, HT (ASCP) Editor. The Blakston Division McGraw-Hill Book Company, New York; *The Armed Forces Institute of Pathology Advanced Laboratory Methods in Histology and Pathology* (1994) Ulreka V. Mikel, Editor. Armed Forces Institute of Pathology, American Registry of Pathology, Washington, D.C.]. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, the tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De (CMS, Houston, Tex.) may be used.

Morphological Staining

After deparaffinization, the sections mounted on slides may be stained with a morphological stain for evaluation. The morphological stain to be used in the instant method provides for accurate morphological evaluation of a tissue section and also allows for accurate quantification of fluorescently labeled (e.g., SPECTRUM ORANGE® and SPECTRUM GREEN®) nucleic acid probes when the sections are subsequently processed for FISH. Many morphological stains fluoresce when illuminated by light of the same wavelength required to visualize the probe fluorophore of interest. The disclosed method solves this problem. Generally, the section is stained with one or more dyes each of which distinctly stains different cellular components. In a preferred embodiment xanthine dye or the functional equivalent thereof and/or a thiazine dye or the functional equivalent thereof are used to enhance and make distinguishable the nucleus, cytoplasm, and "granular" strictures within each. Such dyes are commercially available and often sold as sets. By way of example, HEMA 3® (CMS, Houston, Tex.) stain set comprises xanthine dye and thiazine dye. Methylene blue may also be used. Examples of other morphological stains that may be used on the instant method include, but are not limited to, dyes that do not significantly autofluoresce at the same wavelength as fluorescent label(s) used for the subsequent FISH analysis. For example, where the fluorescent labels used for the FISH are SPECTRUM ORANGE® and SPECTRUM GREEN®, the morphological stain preferably does not significantly fluoresce at about 509/538 (peak excitation/emission) and/or about 559/588 (peak excitation/emission). One of skill in the art will appreciate that staining may be optimized for a given tissue by increasing or decreasing the length of time the slides remain in the dye.

After staining, the tissue section may be analyzed by standard techniques of microscopy. Generally, a pathologist or the like assesses the tissue for the presence of abnormal or normal cells or a specific cell type and provides the loci of the cell types of interest. Thus, for example, in a study correlating HER2/neu amplification in breast cancer, a pathologist or the like would review the slides and identify normal breast cells and abnormal breast cells (See e.g. Example 2).

Any means of defining the loci of the cells of interest may be used (e.g., coordinates on an X-Y axis). Generally, after light microscopy and prior to the FISH procedure, the slides are destained by conventional methodology. The present method provides an advantage over the prior procedures in the art in that no separate destaining procedure is required prior to FISH. Avoidance of a destaining step is actually preferred in order to protect the integrity of the DNA for in situ hybridization.

Immunohistochemistry (IHC)

Prior to FISH, the Tissue section may be subjected to IHC. IHC may be performed in combination with morphological staining as discussed in the preceding section (either prior to, but preferably thereafter).

Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromagenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in Current Protocols in Immunology, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et ail. Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor [e.g., orthophenylene diamine (OPD) or 3,3', 5,5'-tetramethyl benzidine hydrochloride (TMB)];

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out [see, e.g., Leong et al. *Appl. Immunohistochem.* 4(3):201 (1996)].

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation.

The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope.

Where the antigen is HER2 protein, staining intensity criteria may be evaluated as follows:

TABLE 1

HER2 Protein Staining Intensity Criteria

| Staining Pattern | Score |
|---|---|
| No staining is observed in tumor cells. | 0 |
| A faint/barely perceptible membrane staining is detected in tumor cells. The cells are only stained in part of their membrane. | 1+ |
| A weak to moderate complete membrane staining is observed in tumor cells. | 2+ |
| A moderate to strong complete membrane staining is observed in tumor cells. | 3+ |

In this embodiment of the invention, it may be desirable to select a subgrouping of the tissue samples subjected to IHC for further analysis by FISH. For example, tissue samples with 1+ and 2+ scores, and especially, the 2+ subgroup may be subjected to further FISH as explained below.

Fluorescence In Situ Hybridization (FISH)

In, situ hybridization is generally carried out on cells or tissue sections fixed to slides. In situ hybridization may be performed by several conventional methodologies [See for e.g. Leitch et al. *In Situ Hybridization: a practical guide*, Oxford BIOS Scientific Publishers, Micropscopy handbooks v. 27 (1994)]. In one in situ procedure, fluorescent dyes [such as fluorescein isothiocyanate (FITC) which fluoresces green when excited by an Argon ion laser] are used to label a nucleic acid sequence probe which is complementary to a target nucleotide sequence in the cell. Each cell containing the target nucleotide sequence will bind the labeled probe producing a fluorescent signal upon exposure, of the cells to a light source of a wavelength appropriate for excitation of the specific fluorochrome used.

Various degrees of hybridization stringency can be employed. As the hybridization conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration may also increase the effective concentration of labeled probe to increase the rate of hybridization and ultimate signal intensity. After hybridization, slides are washed in a solution generally containing reagents similar to those found in the hybridization solution with washing time varying from minutes to hours depending on required stringency. Longer or more stringent washes typically lower nonspecific background but run the risk of decreasing overall sensitivity. Exemplary in situ hybridization conditions for detecting HER2/neu amplification in breast tissue are shown in Example 2.

Probes used in the FISH analysis may be either RNA or DNA oligonucleotides or polynucleotides and may contain not only naturally occurring nucleotides but their analogs like digoxygenin dCTP, biotin dcTP 7-azaguanosine, azidothymidine, inosine, or uridine. Other useful probes include peptide probes and analogues thereof, branched gene DNA, peptidometics, peptide nucleic acid (PNA) and/or antibodies.

Probes should have sufficient complementarity to the target nucleic acid sequence of interest so that stable and specific binding occurs between the target nucleic acid sequence and the probe. The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention [see for e.g. Sambrook, J., Fritsch, E. F., Maniatis, T., *Molecular Cloning A Laboratory Manual*, Cold Spring Harbor Press. (1989)].

One of skill in the art will appreciate that the choice of probe will depend on the genetic abnormality of interest. Genetic abnormalities that can be detected by this method include, but are not limited to, amplification, translocation, deletion, addition and the like. Examples of amplification include, but are not limited to, HER2/neu in breast and ovarian cancer, N-myc in neuroblastoma, C-myc in small cell lung cancer. Examples of abnormal chromosome number include, hut are not limited to, trisomy 8 in leukemia, monosomy 7 in myloproliferative disorders, and trisomy 12 in chronic lymphoblastic leukemia. Examples of translocations include, but are not limited to, bcr/abl [t (9; 22)] translocation in chronic mylogenous leukemia and the t (15; 17) translocation FAB-M3 (acute promyelocytic leukemia). Examples of deletions include EGFR vIII and p53. By way of example for evaluating HER2/neu amplification a probe spanning a 140 kb region on the long arm of chromosome 17 containing the HER2/neu gene (17q11.2-17q12) may be used. A probe for the α-satellite sequences in the centromeric region of chromosome 17(D1721) may be used to evaluate for aneusomy of chromosome 17 as a source or cause for HER2/neu amplification. For example, a cocktailed version of these probes may be obtained from Vysis, Inc. where each probe is directly labeled with easily distinguishable fluorophores, such as SPECTRUM ORANGE® and SPECTRUM GREEN®.

Probes may also be generated and chosen by several means including, but not limited to, mapping by in situ hybridization, somatic cell hybrid panels, or spot blots of sorted chromosomes; chromosomal linkage analysis; or cloned and isolated from sorted chromosome libraries from human cell lines or somatic cell hybrids with human chromosomes, radiation somatic cell hybrids, microdissection of a chromosome region, or from yeast artificial chromosomes (YACs) identified by PCR primers specific for a unique chromosome locus or other suitable means like an adjacent YAC clone. Probes may be genomic DNA, cDNA, or RNA cloned in a plasmid, phage, cosmid, YAC, Bacterial Artificial Chromosomes (BACs), viral vector, or any other suitable vector. Probes may be cloned or synthesized chemically by conventional methods. When cloned, the isolated probe nucleic acid fragments are typically inserted into a vector, such as lambda phage, pBR322, M13, or vectors containing the SP6 or T7 promoter and cloned as a library in a bacterial host. [See for e.g. Sambrook, J., Fritsch, E. F., Maniatis, T., *Molecular Cloning A Laboratory Manual*, Cold Spring Harbor Press, (1989)].

Probes are preferably labeled with a fluorophor. Examples of fluorophores include, but are not limited to, rare earth chelates (europium chelates), Texas Red, rhodamine, fluorescein, dansyl, Lissamine, umbelliferone, phycocryrtherin, phycocyanin., or commercially available fluorophors such SPECTRUM ORANGE® and SPECTRUM GREEN® and/or derivatives of any one or more of the above. Multiple probes used in the assay may be labeled with more than one distinguishable fluorescent or pigment color. These color differences provide a means to identify the hybridization positions of specific probes. Moreover, probes that are not separated spatially can be identified by a different color light or pigment resulting from mixing two other colors (e.g., light red+green=yellow) pigment (e.g., blue+yellow=green) or by using a filter set that passes only one color at a time.

Probes can be labeled directly or indirectly with the fluorophor, utilizing conventional methodology. Additional probes and colors may be added to refine and extend this general procedure to include more genetic abnormalities or serve as internal controls. By way of example the HER2/neu gene is in chromosome 17, and as an internal control a probe for α-satellite sequences specific for chromosome 17 (D17Z1) may be used (Vysis. Inc.) to prove diploidy in areas of non-malignant cells and/or to establish the presence or absence of chromosome 17 aneusomy in areas of HER2/neu amplification.

After processing for FISH, the slides may be analyzed by standard techniques of fluorescence microscopy [see for e.g. Ploem and Tanke *Introduction to Fluorescence Microscopy*, New York, Oxford University Press (1987)]. Briefly, each slide is observed using a microscope equipped with appropriate excitation filters, dichromic, and barrier filters. Filters are chosen based on the excitation and emission spectra of the fluorochromes used. Photographs of the slides may be taken with the length of time of film exposure depending on the fluorescent label used, the signal intensity and the filter chosen. For FISH analysis the physical loci of the cells of interest determined in the morphological analysis are recalled and visually conformed as being the appropriate area for FISH quantification.

In order to correlate cellular morphology and/or IHC with FISH, one may use a computer-driven, motorized stage which stores location of co-ordinates. This may be used to evaluate the same area by two different analytical techniques. For example, color images of the morphologically stained areas may be captured and saved using a computer-assisted cooled CCD camera. The same section may be subsequently taken through the FISH procedure, the stored locations recalled, and the designated areas scored for the presence of fluorescent nuclear signals. A similar procedure for IHC followed by FISH is contemplated.

Typically, hundreds of cells are scanned in a tissue sample and quantification of the specific target nucleic acid sequence is determined in the form of fluorescent spots, which are counted relative to the number of cells. Deviation of the number of spots in a cell from a norm (e.g., such as probing for the HER2/neu gene in a normal cell will produce two copies, abnormal greater than two) may be indicative of a malignancy or a predisposition to a malignancy, disease, or other abnormality. The relative number of abnormal cells to the total cell sample population may also indicative of the extent of the condition or abnormality. In addition, using family health histories and/or genetic screening, it is possible to estimate the probability that a particular subject has for developing certain types of cancer. Those subjects that have been identified as being predisposed to developing a particular form of cancer can be monitored or screened to detect early evidence of disease. Upon discovery of such evidence, early treatment can be undertaken to combat the disease. Similarly, those subjects who have already developed a malignancy and who have been treated to remove the cancer or are otherwise in remission are particularly susceptible to relapse and reoccurrence, including the metastasis of tumors. Such subjects can be monitored and screened using the presently disclosed methods to detect evidence of metastasis and upon discovery of such evidence, immediate treatment can be undertaken to combat the disease.

Kits

In yet another embodiment, this invention provides a kit comprising a fluorescently labeled probe specific for the target nucleic acid sequence of interest and a morphological stain and/or an antibody which specifically binds target antigen. The kit further comprises a set of instructions for applying the stain or antibody and probe to the same section of a tissue sample. By way of example, the fluorescently labeled probe may be complementary to the HER2/neu gene and the morphological stain may be HEMA 3® (CMS, Houston, Tex.). Ally fluorescent label as described above may be used to label the probe. The IHC/FISH kit may comprise a fluorescently labeled probe complementary to the HER2/neu gene and an antibody (e.g. polyclonal antibody) which binds to the HER2 protein. The kit may include both a primary and secondary antibody, wherein the secondary antibody is conjugated to a label, e.g., an enzymatic label. The invention also provides an IHC kit which has instructions to perform FISH on the same section of tissue sample on which IHC has been previously performed.

Other optional components in the kit include one or more buffers (e.g., block buffer, wash buffer, substrate buffer, etc), other reagents such as substrate (e.g., chromagen) which is chemically altered by an enzymatic label, epitope retrieval solution, control samples (positive and/or negative controls), control slide(s) etc.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Evaluation of Morphological Stains on FISH Analysis

A sensitive and specific evaluation of breast tumors for the amplification of HER2/neu by FISH requires definitive identification and scoring of invasive ductal carcinoma cells as distinct from other stromal and inflammatory elements found in the biopsy. Thus it was necessary to identify a stain which would allow for complete morphological evaluation of the tissue, and which also allowed for easy quantification of nuclear signals upon subsequent hybridization with fluorescently labeled nucleic acid probes. Many morphological stains fluoresce when illuminated by light of the same wavelength required to visualize the probe fluorophores of interest. When this autofluorescence is of a color similar to that of the probe fluorophore, signal quantification is made difficult.

Results from the evaluation of six commonly used morphological stains may be found in Table 2.

TABLE 2

Evaluation of Morphological Stains

| Morph. stain | Morphology | Autofl. pre-FISH | DAPI | Chr 17 | HER2/neu | Autofl. post-FISH | Comments |
|---|---|---|---|---|---|---|---|
| Paragon (Toludine blue/basic fuchsin) | Acceptable | Bright red | Visible | Visible | Visible | Bright red | Red autofluoresence may interfere with FISH |
| MGP | Not acceptable | Intense red | ND | ND | ND | ND | Red autofl. great |
| Gill Hematoxylin | Not acceptable | Mod red Mod green | Visible | Visible | Visible | Mod red | Autofl. may interfere with FISH |
| Weigert | Acceptable | Dull red Dull green | Visible | Visible | Visible-dim | Mod red | Post-FISH autofl. masks HER2/neu |
| Methylene blue | Acceptable | Mod orange | Visible | Visible | Visible | Mod orange | Possible candidate |
| HEMA 3 ® (destain) | Acceptable | Dim green | Absent | Absent | Absent | NA | Destaining may have interfered with FISH |
| HEMA 3 ® (w/o destain) | Acceptable | Dim green | Visible | Visible | Visible | Trace-green | Good candidate |

Methyl green pyronin (MGP) and Gill hematoxylin were not analyzed further due to poor morphological definition. Paragon (toluidine blue/basic fuchsin) and Weigert were eliminated from consideration because of an unacceptably high level of red or orange autofluorescence which masked the orange HER2/neu signals in the nucleus. Methylene blue yielded acceptable morphological staining, but demonstrated orange autofluorescence which caused moderate difficulty in visualizing HER2/neu signals. This stain was considered a possible candidate. HEMA 3®, however, was superior in that it provided good morphological detail and showed only modest dim green autofluorescence which did not interfere to any extent with FISH evaluation. An initial attempt at destaining HEMA 3® prior to FISH was found to damage the integrity of the DNA in the cells and ultimately proved to be unnecessary anyway. It was possible for the stained tissue to be taken directly through the FISH procedure without intermediate processing, yielding high-quality nuclear signals without any negative consequence. HEMA 3®, therefore, met all essential requirements and was the stain of choice for the proposed system. Unless otherwise indicated, the tissues and FISH analysis were conducted as discussed in Example 2.

Example 2

Detection and Quantification of HER2/neu Amplification in Breast Tissue

Materials and Methods

Tissue Specimens and Preparation for FISH

Five micron sections were cut from breast tissue which had been fixed in buffered formalin and embedded in paraffin. Sections were placed on positively charged Superfrost Plus slides (CMS, Houston, Tex.) which had also been treated with poly-L-lysine or were mounted on positively charged slides which had no additional treatment prior to the mounting of the slides. Some material had been archived for up to fourteen years. Slide mounted tissue sections were heated on a 65° C. slide warmer for approximately 3 seconds, placed on the bench top for 2 seconds, and deparaffinized in Hemo-De (CMS Houston, Tex.) for 1(0 minutes, ×3, followed by immersion in 100% ethanol (EtOH) for 5 minutes, ×2. Slides were air dried in a vertical position. Those slides to be stained for morphologic evaluation were dipped in HEMA 3® Solution I (CMS, Houston, Tex.) for one second, ×3, then immediately dipped in HEMA 3® Solution II for one second, ×3. Each slide was rinsed in deionized, distilled water and allowed to air dry in a vertical position. The slides were mounted and coverslipped using an aqueous-based mounting medium (Biomeda Corporation, Foster City, Calif.) for evaluation at the microscope. Areas of interest identified by the pathologist were marked on the coverglass and subsequently circled on the underside of the slide using a diamond-tipped pencil. The coverglass was removed by placing the slide in a water-filled Coplin jar, which had been pre-heated in a 73±2° C. waterbath, for approximately 15-30 minutes, or until the coverglass slipped off. The section was dehydrated in 70% EtOH for 3 minutes, 85% EtOH for 3 minutes, and 100% EtOH for 3 minutes. These slides, and any deparaffinized sections that were not stained but were to be processed by FISH, were immersed in a sodium isothiocyanate Pretreatment Solution (Vysis, Inc., Downers Grove, Ill.) for 30 minutes at 80±10° C. The sections were washed in deionized water for one minute, then in Protease Wash Buffer (2×SSC, pH 7.4, Vysis, Inc.) for 5 minutes at room temperature, ×2. The sections were treated in Protease Solution (Vysis, Inc.) for 10 minutes at 37° C. Following protease digestion, the sections were washed in Protease Wash Buffer for 5 minutes, ×2, and dried on a 45-50° C. slide warmer for 2-5 minutes.

Probes

A probe spanning approximately 140 kb of the region on the long arm of chromosome 17 containing the HER2/neu proto-oncogene (17q11.2-17q12) was utilized to detect the presence or absence of HER2/neu amplification. Chromosome 17 aneusomy of the cell was evaluated using an α-satellite sequence probe (D17Z1) specific for the centromere of chromosome 17 (CEP 17). The probes were provided by Vysis, Inc. in an optimized cocktail mixture where the HER2/neu probe is directly labeled with the fluorophore SPEC- TRUM ORANGE® (peak excitation/emission=559/588) and the CEP 17 probe is directly labeled with the fluorophore SPECTRUM GREEN® (peak excitation/emission=509/538) (Vysis, Inc.).

In Situ Hybridization

The pre-treated (see above) slide-mounted sections were immersed in Denaturation Solution (70% formamide/2×SSC, pH 7.0) for 5 minutes at 73±1° C. Sections were then dehydrated in 70% EtOH for one minute, 85% EtOH for one minute, and 100% EtOH for one minute. Drained slides were placed on a 45-50° C. slide warmer for 2-5 minutes just before application of the hybridization mixture. This mixture was prepared as directed by VYSIS® protocol. The probe solution was denatured by incubation in a 73° C. waterbath for 5 minutes. Following brief centrifugation, 10 μL of the solution was pipetted onto each section, a coverslip applied, and the edges sealed with rubber cement. Hybridization was carried out in a humidified box overnight (14-18 h) in a 37° C. incubator. The rubber cement was carefully removed and the slides immersed in room temperature Wash Buffer I (0.4× SSC/0.3% NP-40) until the coverslip floated off. Slides were drained of excess liquid by blotting the edges on a paper towel, then placed in a Coplin jar of Wash Buffer I, which had been prewarmed to 72±10° C., for 2 minutes. Sections were washed in room temperature Wash Buffer II (2×SSC/0.1% NP-40) for one minute, drained vertically on paper towels, and allowed to air-dry in darkness being careful not to overdry. Once slides were dry, 15 μL of DAPI counterstain (a mixture of equal parts DAPI I and DAPI II, Vysis, Inc.) was pipetted onto the hybridization area. A coverglass was added and the edges sealed with clear nail polish. Slides were analyzed immediately or stored in the dark at −20° C.

Controls

Cultured cell lines SKBR3, MDA175, and MDA231 were harvested, formalin-fixed, and paraffin-embedded for use as highly amplified, barely amplified, and non-amplified controls, respectively. These cell lines were used in the evaluation of the morphological stains. The presence of appropriate nuclear FISH signals served to assure that the reagents and procedure involved in the devised methodology worked properly.

Microscopy

An Olympus BX60 epifluorescence microscope equipped with a 100 watt mercury-arc lamp, a 40×UPlanApo objective, and a 100×UPlanFl objective was used. The filter slider was built by Chroma Technology Corporation (Brattleboro, Vt.) for Olympus and included three single band pass filters optimized for visualization of DAPI, FITC, and Texas Red fluorochromes, a dual-band pass filter optimized for FITC and Texas Red, and a triple-band pass filter optimized for DAPI, FITC, and Texas Red. The microscope was also equipped with 4×, 10×, 20×, and 40×UPlanFl objectives for use in transmittance light microscopy. A BioPoint X,Y (Ludl Electronic Products, Ltd., Hawthorne, N.Y.) computer-driven motorized stage was used for storage and retrieval of physical locations. Images were acquired using a CoolCam 2000 3-chip color cooled CCD camera (Sci-Measure, Atlanta, Ga.) and printed using a Tektronix Phaser 440 dye sublimation printer (Tektronix, Inc., Wilsonville, Oreg.).

FISH Scoring Criteria

After FISH processing, tissue sections were scanned using the 40× objective to evaluate for tissue loss and to ensure that hybridization was uniform across the section. Morphologically identified areas of normal or tumor tissue were located on FISH processed slides by recalling stored x and y coordinates. Alternatively, if location coordinates had not been stored, a saved morphological image (HEMA 3® stain) of the area of interest was used as a reference to localize the appropriate area after FISH processing. Signals were enumerated using the 100× objective, switching between different filters to optimize signal discrimination. Nuclear boundaries were defined by DAPI excitation. Only those nuclei were scored which could be clearly identified as intact and non-overlapping. The presence of nuclei having no CEP 17 or no HER2/neu signaled the possibility of a hybridization failure or the existence of truncated nuclei, suggesting an unacceptably thin section. The hybridization quality of the entire section was assessed completely before making a decision regarding acceptability. In cases of high HER2/neu gene amplification (>10-20 signals per nucleus), signals were often coalesced into clusters and could not be precisely enumerated. If, as in some instances, the CEP 17 signals appeared fragmented, a broken signal was scored as two separate signals if the distance between them was of sufficient size that a third comparable signal could be passed through it. A minimum scoring goal of 100 nuclei per area was attempted; however, in certain circumstances, it was not possible to meet this goal. For example, areas of normal tissue tended to be minimally represented and relatively non-cellular; in these situations, all clearly discernible cells were scored. In areas of highly amplified HER2/neu, a total of 30-40 cells was considered adequate to establish amplification status.

Immunohistochemical Staining

Sections cut serially from those used for FISH analysis were immunohistochemically stained using a murine monoclonal antibody against HER2 [4D5; Fendly et al. *Cancer Research* 50:1550-1558 (1990)]. Slide-mounted sections were placed into xylenes 3×, 10 minutes each time, then dehydrated in absolute ethanol 2×, 5 minutes each. Endogenous peroxidase activity was quenched by placing the slides in a 0.3% solution of hydrogen peroxide in methanol. The sections were then serially rehydrated in 95% ethanol for 5 minutes, followed by 80% ethanol for 5 minutes. Sections were incubated briefly in the buffer routinely used with the Ventana ES automated immunostaining instrument. The staining program began with a 4 minute protease treatment. Incubation with the primary antibody (10 μg/ml) proceeded for the maximum allowable time period, 32 minutes. The detection system employed a biotin/avidin reaction using DAB and a hematoxylin counterstain. After staining and detection, the sections were dehydrated in a graded series of ethanol into xylenes in preparation for permanent coverslipping.

Immunohistochemistry Scoring Criteria

The immunohistochemical staining was interpreted by a breast tumor pathologist and the results assigned to one of four categories defined in the following way: negative/weak, cytoplasmic, 1+, 2+. The second category was reserved for those cells in which staining occurred only in the cytoplasm. The latter two categories applied to cell surface antibody staining. Images of immunostained sections representative of each category were captured using the CCD camera. Attempts were made to relocate areas that had been scored for FISH on the corresponding serial section, and whenever possible that image was captured.

Specimens

Formalin-fixed, paraffin-embedded human breast tissue was obtained through clinical submission of specimens to Cytometry Associates and Vanderbilt University Medical Center (VUMC), Department of Pathology. Some materials may have been archived at VUMC for up to fourteen years. In some cases, the specimens were identified for the study based on the likelihood of HER2 amplification as predicted by IHC results or hormone receptor status. Other cases were known to be disease-free based on morphological evaluation at VUMC.

Stain Plus FISH vs. FISH only

Figure 2:
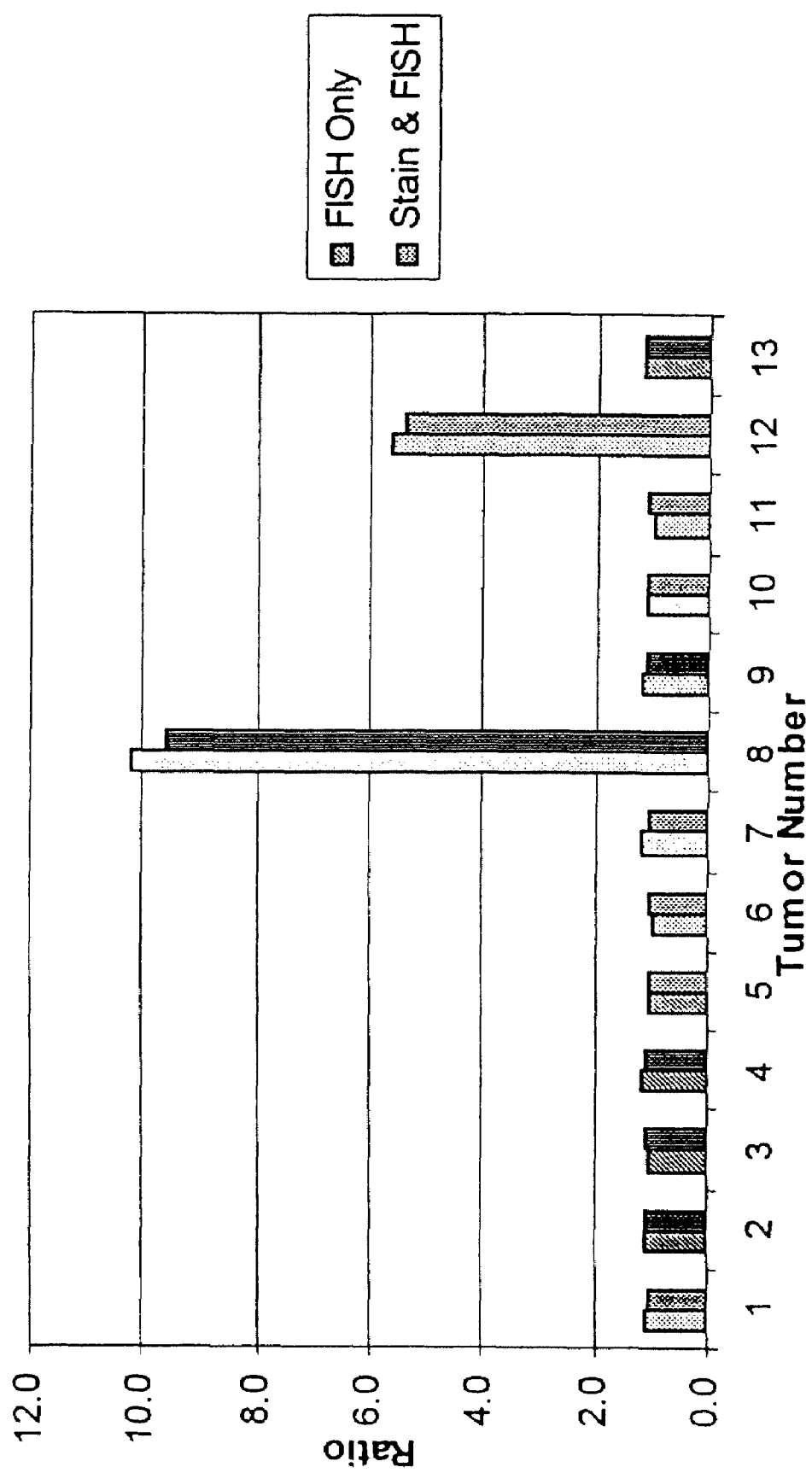
FIG. 2 shows the effect of HEMA 3® morphologic stain on FISH with respect to tumor biopsy sections. Duplicate sections from 13 tumor specimens were analyzed for HER2 and chromosome 17 (Chr 17) by FISH either with or without prior staining for morphologic analysis prior to FISH. The same area of tumor was scored for FISH on each section.

Initially, the effect of HEMA 3® stain on the ability to score FISH was evaluated in formalin-fixed, paraffin-embedded cells harvested from each of three cell-lines of known HFR2/neu amplification status (FIG. 1). Results from analysis by two individuals were comparable and successfully identified the different cell-lines as being of the appropriate, expected amplification status. The stain had no adverse effect on FISH quantification in these cell lines. A total of 10 patient specimens was included in the study comparing stained and hybridized tissue versus tissue which was hybridized without prior staining. The same areas of tumor and normal cells identified on each of two serial sections was analyzed for the presence of HER2/neu and chromosome 17 by FISH either with or without prior morphological staining. Two analysts performed FISH quantification of the designated areas. Mean HER2/neu:Chr17 ratios for each of the areas of tumor in the ten patient specimens scored, plus the three cell lines, are shown in FIG. 2. There was no statistically significant quantitative difference as a result of the two different treatments of the tissue sections in either the tumor areas (P=0.196) or the normal areas (P=0.597) scored. The differences in the mean values between the two analysts performing FISH quantification were not statistically significant in areas of either normal cells (P=0.065) or tumor cells (P=0.459). In addition, the inter-observer effect did not depend on which treatment the tissue section had undergone, whether in areas of normal morphology (P=0.513) or in areas of invasive carcinoma (P=0.971).

Blinded vs Non-Blinded Study

Figure 3:
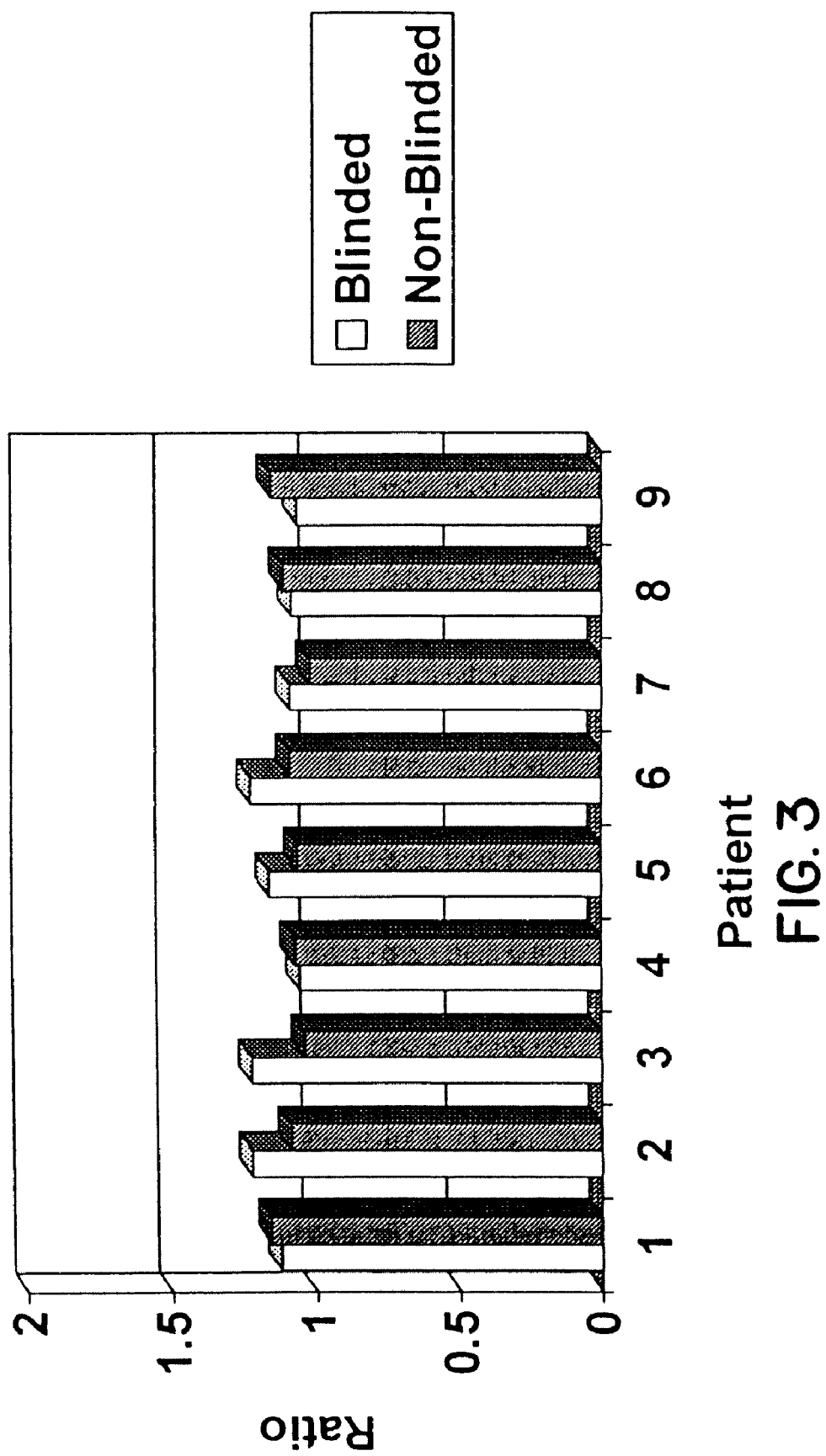
FIG. 3 shows the mean HER2/neu:Chr 17 ratio for blinded vs non-blinded assessment of normal tissue.
Figure 4:
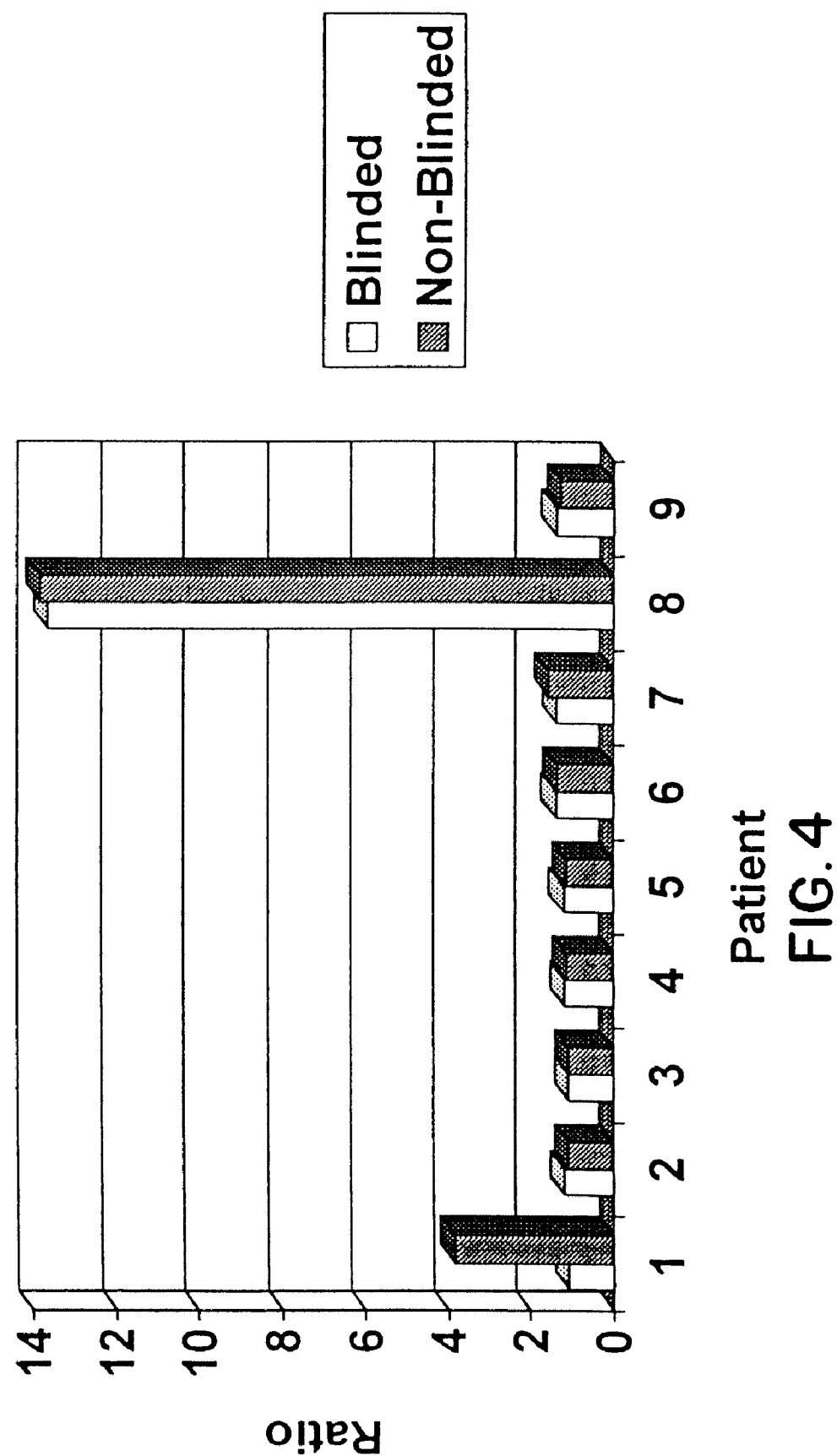
FIG. 4 shows the mean HER2/neu:Chr 17 ratio for blinded vs non-blinded assessment of tumor tissue.

A study was designed to determine whether prior knowledge of morphological cell type biased the scoring of FISH signals. Ten patient specimens included in the study were stained with HEMA 3® for morphological evaluation by a pathologist. Areas of normal cellular tissue and areas of invasive carcinoma were identified, their x/y coordinates stored, and images captured and saved. The files were named and stored in an anonymous and random manner so that the two analysts who scored the areas for FISH signals were unaware of their identity or cell type. After the blinded evaluation was completed, the analysts were given a second list of file names of the same ten images and locations of normal and tumor areas, but in this case, the identity and cell type was provided. To score FISH signals, the analyst used the x/y coordinate provided to relocate the area of interest and used the saved image to confirm accurate relocation. The mean HER2/neu:Chr 17 ratio was determined for each area scored by the analysts, and the mean ratio of the two analysts calculated. Mean ratios for blinded vs non-blinded assessment of both normal tissue and tumor tissue are shown in FIGS. 3 and 4, respectively.

Non-Diseased Normal vs Patient Normal

Normal range data were generated from analysis of histologically normal breast tissue obtained from mammoplasty surgical procedures. Ten biopsies were evaluated by two analysts for quantitative detection of HER2/neu and chromosome 17 by FISH. The mean HER2/neu:Chr 17 ratio for the two analysts was 1.07. In order to establish a normal range, areas of normal cellular tissue were identified in 38 biopsies of breast tissue from patients diagnosed with invasive carcinoma. The mean ratio for these specimens was also 1.07. Statistical treatment of the data with a two way repeated measures ANOVA found no significant difference between the two tissue types (P=0.821). Normal range values ($\geq 0.9$ and $\leq 1.2$) were established based on the diseased normal data, setting upper and lower limits by calculating two standard deviations from the mean (Table 3).

TABLE 3

Normal Range Determinations

| Tissue | Mean Ratio | n | Range |  |  |  |  |  |
|---|---|---|---|---|---|---|---|---|
|  |  |  | 1 SD |  | 2 SD |  | 3 SD |  |
| Non-disease | 1.07 | 20 | 1.06 | 1.09 | 1.04 | 1.11 | 1.02 | 1.13 |
| Disease | 1.07 | 78 | 0.99 | 1.15 | 0.91 | 1.23 | 0.83 | 1.32 |

Definition of a normal range creates a threshold for determining amplification status for HER2/neu. In addition, correlation between normal values derived from non-diseased and diseased tissue provides justification for use of a morphologically normal cellular area in a tumor biopsy as an internal biological control for specificity in that specimen.

Patient Cohort

Using the described system combining morphological staining and FISH, a total of 46 cases of known invasive breast carcinoma were evaluated. Serial sections from each were stained immunohistochemically with the 4D5 antibody to HER21/neu for comparative purposes. HER2/neu and chromosome 17 fluorescent nuclear signals were scored by two analysts and the mean ratios calculated. Ratios for HER2/neu amplification were assigned to one of two ranges either moderately amplified borderline or highly amplified. The lower limit of the moderate amplification range (1.3) was established statistically by determining at what value the ratio differed significantly from normal. The upper limit for moderately amplified status (2.0) was taken from previously published data which defined true amplification as having a ratio of >2.0 [Pauletti et al. *Oncogene* 13:63-72 (1996)]. The relationship between the scoring systems used for HER2/neu amplification by FISH and overexpression by IHC is depicted in Table 4.

TABLE 4

Scoring System for HER2 Amplification/Expression

| HER2 Amplification/Expression | IHC score | FISH ratio |
|---|---|---|
| Negative | Negative | 0.9-1.2 |
| Borderline | 1+ | 1.3-2.0 |
| Amplified | 2+ | >2.0 |

Immunohistochemistry scores were based on membrane staining only; specimens which exhibited cytoplasmic staining (n=4) were excluded from the study data. Correlations between FISH mean ratios and immunohistochemistry scores showed a positive correlation coefficient (0.760) and a low P value (<0.001). Both techniques identified unambiguous amplification or overexpression of HER2/neu equally well with two exceptions (FIG. 5). One case which produced an IHC score of 2+ fell into the moderately amplified range by FISH (ratio=1.7), and one case which showed high amplification by FISH (ratio=9.8) had an IHC score of 1+. FISH quantification of HER2/neu placed ten specimens in the moderate amplification range. Immunohistochemical evaluation identified only four specimens showing moderate positivity (score of 1+), suggesting a less than optimal sensitivity associated with the hum4D5-8 antibody.

Although the present invention has been described in some detail by way of illustration for the purposes of clarity of understanding, it will be apparent that certain changes and modifications may be practiced within the scope of the appended claims. Such modifications which may be apparent to a person skilled in the art are intended to be within the scope of the invention.

What is claimed is:

1. A method for detecting the presence of a cellular target protein and a cellular target nucleic acid in a locus of interest in a tissue sample containing cells of interest, wherein said cells of interest may comprise normal cells or may comprise abnormal cells, or both, and said locus of interest comprises a region containing cells of interest, said method comprising the steps of: (a) applying a morphological stain to a tissue sample effective to provide a stained tissue sample; (b) identifying a locus of interest in said stained tissue sample; (c) contacting a section of the tissue sample with an antibody which specifically binds to the target protein, wherein said section includes said locus of interest; (d) determining binding of the antibody to the section of tissue sample; (e) hybridizing a labeled nucleic acid probe to the target nucleic acid in the same section of tissue sample which includes the locus of interest; (f) detecting the presence of the labeled nucleic acid probe in the section of tissue sample; and (g) comparing the results of step (d) with the results of step (f), wherein the morphological stain used in step (a) does not significantly interfere with detection of the labeled nucleic acid probe used in step (e).

2. The method of claim 1 wherein the label is a label selected from the group consisting of a fluorescent dye, a colloidal gold particle, a radioisotope label, and an enzyme substrate label.

3. The method of claim 1, wherein the nucleic acid probe is constructed to hybridize to the target nucleic acid sequence indicating a genetic abnormality selected from the group consisting of amplification, addition, substitution, translocation and deletion.

4. The method of claim 1, wherein the target nucleic acid is selected from the group consisting of HER2/neu gene and the centromere of chromosome 17.

5. The method of claim 1, wherein the target protein is a HER2 protein.

6. The method of claim 1, wherein the tissue sample is selected from the group consisting of breast, prostate, ovary, colon, lung, endometrium, stomach, salivary gland and pancreas tissue samples.

7. The method of claim 1, wherein the section of tissue sample is obtained from fixed, paraffin-embedded tissue sample.

8. The method of claim 1, wherein the label is a radioisotope label selected from the group consisting of $^{35}$S, $^{14}$C, $^{125}$I, $^{3}$H, and $^{131}$I.

9. The method of claim 1, wherein the label is an enzyme substrate label selected from the group of enzyme substrate labels consisting of horseradish peroxidase (HRPO), alkaline phosphatase (AP), and β-D-galactosidase (β-D-Gal).

10. The method of claim 1, wherein the label is a fluorescent dye selected from the group consisting of Texas Red, fluorescein, phycocrytherin, rhodamine, phycocyanin, dansyl, umbelliferone, SPECTRUM GREEN®, and SPECTRUM ORANGE®.

11. A method for detecting the presence of a cellular target protein and a cellular target nucleic acid in a locus of interest in a tissue sample containing cells of interest, wherein said cells of interest may comprise normal cells or may comprise abnormal cells, or both, and said locus of interest comprises a region containing cells of interest, said method comprising the steps of: (a) applying a morphological stain to a tissue sample effective to provide a stained tissue sample; (b) identifying a locus of interest in said stained tissue sample; (c) contacting a section of the tissue sample with an antibody which specifically binds to the target protein, wherein said section includes said locus of interest; (d) determining binding of the antibody to the section of tissue sample; (e) hybridizing a labeled nucleic acid probe to the target nucleic acid in the same section of tissue sample which includes the locus of interest; (f) detecting the presence of the labeled nucleic acid probe in the section of tissue sample; and (g) comparing the results of step (d) with the results of step (f), wherein autofluorescence of the morphological stain used in step (a) does not significantly interfere with detection of the labeled nucleic acid probe used in step (e).

12. The method of claim 11 wherein the label is a fluorescent dye.

13. The method of claim 11, wherein the nucleic acid probe is constructed to hybridize to the target nucleic acid sequence indicating a genetic abnormality selected from the group consisting of amplification, addition, substitution, translocation and deletion.

14. The method of claim 11, wherein the target nucleic acid is selected from HER2/neu gene and the centromere of chromosome 17.

15. The method of claim 11, wherein the target protein is a HER2 protein.

16. The method of claim 11, wherein the tissue sample is selected from the group consisting of breast, prostate, ovary, colon, lung, endometrium, stomach, salivary gland and pancreas tissue samples.

17. The method of claim 11, wherein the section of tissue sample is obtained from fixed, paraffin-embedded tissue sample.

18. A method for detecting the presence of a cellular target protein and a cellular target nucleic acid in a locus of interest in a tissue sample containing cells of interest, wherein said cells of interest may comprise normal cells or may comprise abnormal cells, or both, and said locus of interest comprises a region containing cells of interest, said method comprising the steps of: (a) applying a morphological stain to a tissue sample effective to provide a stained tissue sample; (b) identifying a locus of interest in said stained tissue sample; (c) contacting a section of the tissue sample with an antibody which specifically binds to the target protein, wherein said section includes said locus of interest; (d) determining binding of the antibody to the section of tissue sample; (e) hybridizing a labeled nucleic acid probe to the target nucleic acid in the same section of tissue sample which includes the locus of interest; (f) detecting the presence of the labeled nucleic acid probe in the section of tissue sample; and (g) comparing the results of step (d) with the results of step (f), wherein the morphological stain used in step (a) does not significantly autofluoresce at the same wavelength as a fluorescent label of the fluorescently labeled nucleic acid probe used in step (e).

19. The method of claim 18 wherein the label is a fluorescent dye.

20. The method of claim 18, wherein the nucleic acid probe is constructed to hybridize to the target nucleic acid sequence indicating a genetic abnormality selected from the group consisting of amplification, addition, substitution, translocation and deletion.

21. The method of claim 18, wherein the target nucleic acid is selected from HER2/neu gene and the centromere of chromosome 17.

22. The method of claim 18, wherein the target protein is a HER2 protein.

23. The method of claim 18, wherein the tissue sample is selected from the group consisting of breast, prostate, ovary, colon, lung, endometrium, stomach, salivary gland and pancreas tissue samples.

24. The method of claim 18, wherein the section of tissue sample is obtained from fixed, paraffin-embedded tissue sample.

* * * * *

UNITED STATES PATENT AND TRADEMARK OFFICE
CERTIFICATE OF CORRECTION

| | | |
|---|---|---|
| PATENT NO. | : 7,674,589 B2 | Page 1 of 1 |
| APPLICATION NO. | : 12/331178 | |
| DATED | : March 9, 2010 | |
| INVENTOR(S) | : Cohen et al. | |

It is certified that error appears in the above-identified patent and that said Letters Patent is hereby corrected as shown below:

TITLE PAGE, item (73) ASSIGNEE, SHOULD READ:

--[73] Assignee: Genentech, Inc., South San Francisco, CA (USA), and Esoterix, Inc., Austin, TX (USA)--.

Signed and Sealed this
Third Day of May, 2011

David J. Kappos
*Director of the United States Patent and Trademark Office*